United States Patent
Nakanishi et al.

(10) Patent No.: US 9,704,223 B2
(45) Date of Patent: Jul. 11, 2017

(54) METHOD AND SYSTEM FOR SUBSTANTIALLY REDUCING CONE BEAM ARTIFACTS BASED UPON ADAPTIVE SCALING FACTOR IN CIRCULAR COMPUTER TOMOGRAPHY (CT)

(71) Applicant: TOSHIBA MEDICAL SYSTEMS CORPORATION, Otawara-Shi, Tochigi-Ken (JP)

(72) Inventors: Satoru Nakanishi, Utsunomiya (JP); Alexander Zamyatin, Hawthorne Woods, IL (US); Be-Shan Chiang, Austin, TX (US)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 317 days.

(21) Appl. No.: 14/300,668

(22) Filed: Jun. 10, 2014

(65) Prior Publication Data

US 2015/0356728 A1 Dec. 10, 2015

(51) Int. Cl.
*G06K 9/00* (2006.01)
*G06T 5/00* (2006.01)
*A61B 6/03* (2006.01)
*A61B 6/00* (2006.01)
*G06T 11/00* (2006.01)

(52) U.S. Cl.
CPC .............. *G06T 5/001* (2013.01); *A61B 6/032* (2013.01); *A61B 6/4085* (2013.01); *A61B 6/5282* (2013.01); *G06T 5/002* (2013.01); *G06T 11/005* (2013.01); *G06T 2207/10081* (2013.01); *G06T 2211/416* (2013.01)

(58) Field of Classification Search
CPC ....... A61B 6/032; A61B 6/4085; A61B 6/466; A61B 6/5217
USPC ....... 382/128, 130, 131, 132, 260, 274, 275; 128/922, 923
See application file for complete search history.

(56) References Cited

U.S. PATENT DOCUMENTS

| | | | | |
|---|---|---|---|---|
| 5,926,521 A * | 7/1999 | Tam | ....... | A61B 6/032 378/15 |
| 6,130,930 A * | 10/2000 | Tam | ....... | A61B 6/032 378/15 |
| 6,333,960 B1 * | 12/2001 | Tam | ....... | A61B 6/032 378/15 |
| 6,842,502 B2 * | 1/2005 | Jaffray | ....... | A61B 6/032 378/19 |

(Continued)

*Primary Examiner* — Yosef Kassa
(74) *Attorney, Agent, or Firm* — Kenichiro Yoshida

(57) ABSTRACT

Cone beam artifacts arise in circular CT reconstruction. The cone beam artifacts are substantially removed by reconstructing a reference image from measured data at circular source trajectory, generating synthetic data by forward projection of the reference image along a pre-determined source trajectory, which supplements the circular source trajectory to a theoretically complete trajectory, reconstructing a correction image from the synthetic data and applying a scaling factor whose value is adaptively determined and optimized based upon the minimization of a predetermined cone beam artifact metric. Ultimately, the cone beam artifact is substantially reduced by generating a corrected image using the reference image and the correction image that has been optimally scaled based upon the adaptively determined scaling factor value.

25 Claims, 8 Drawing Sheets

(56) References Cited

U.S. PATENT DOCUMENTS

| | | | | |
|---|---|---|---|---|
| 7,280,135 B2* | 10/2007 | Kim | ............... | H04N 5/2357 |
| | | | | 348/228.1 |
| 7,471,765 B2* | 12/2008 | Jaffray | ............... | A61B 6/032 |
| | | | | 378/196 |
| 7,826,592 B2* | 11/2010 | Jaffray | ............... | A61B 6/032 |
| | | | | 378/19 |
| 8,135,111 B2* | 3/2012 | Jaffray | ............... | A61B 6/032 |
| | | | | 378/207 |
| 8,363,919 B2* | 1/2013 | Sebok | ............... | G06K 9/3216 |
| | | | | 378/4 |
| 8,520,974 B2* | 8/2013 | Fujita | ............... | G06T 11/005 |
| | | | | 382/128 |
| 8,605,964 B2* | 12/2013 | Fichtinger | ............... | A61B 5/418 |
| | | | | 382/128 |

\* cited by examiner

METHOD AND SYSTEM FOR SUBSTANTIALLY REDUCING CONE BEAM ARTIFACTS BASED UPON ADAPTIVE SCALING FACTOR IN CIRCULAR COMPUTER TOMOGRAPHY (CT)

A related patent application Ser. No. 13/276,841 has been filed on Oct. 19, 2011 for disclosing a method and system for reducing cone beam artifacts.

FIELD OF THE INVENTION

The current invention is generally related to an image processing and system, and more particularly related to substantially reducing artifacts in cone beam Computer Tomography (CT).

BACKGROUND OF THE INVENTION

Cone beam artifacts are a well known problem in computed tomography. The X-ray source cone angle in most advanced CT systems such as Toshiba AquilionONE is quite large, and CFK images tend to suffer cone beam artifacts due to missing data in radon domain.

In one prior art approach, the artifact in circular cone beam CT is substantially removed by applying exact reconstruction based upon a theoretically complete trajectory such as a combination of a circular trajectory and a line trajectory. Although an additional line scan achieves a theoretically complete trajectory with a circular trajectory for exact reconstruction, the additional scan is often either unavailable or impractical to collect. Furthermore, since circular and line data are not simultaneously obtained, any change in motion or agent enhancement between the two scans causes data inconsistency between the two data sets and affect image accuracy. Lastly, the additional scan undesirably exposes a patient to an additional dose of radiation.

For the above reasons, it is of particular interest to accurately reconstruct image volume only from circular data. In another prior art approach, a scanogram is used to estimate line data. Although this approach does not increase patient's radiation dose, cone beam artifacts are still observable after the estimated line data generally helps reduce much of the artifacts. At the same time, any change in motion or agent enhancement is also causing some inaccuracy in the resulted images.

The above related patent application has disclosed another way to estimate the line data based upon a large image that is extended along a predetermined axis so that an improved image is reconstructed from the circular and the estimated line data. The large image also has a field of view (FOV) that is larger than a desired FOV and is extended in the Z direction to generate the extended large image. In reconstructing the improved image, although a scaling factor is optionally used, a value of the scaling factor has been determined prior to the reconstruction.

In the above described techniques, it is still desired to have additional improvement in a system and a method for substantially reducing artifacts in circular cone beam Computer Tomography (CT).

DETAILED DESCRIPTION OF THE EMBODIMENT(S)

Figure 1:
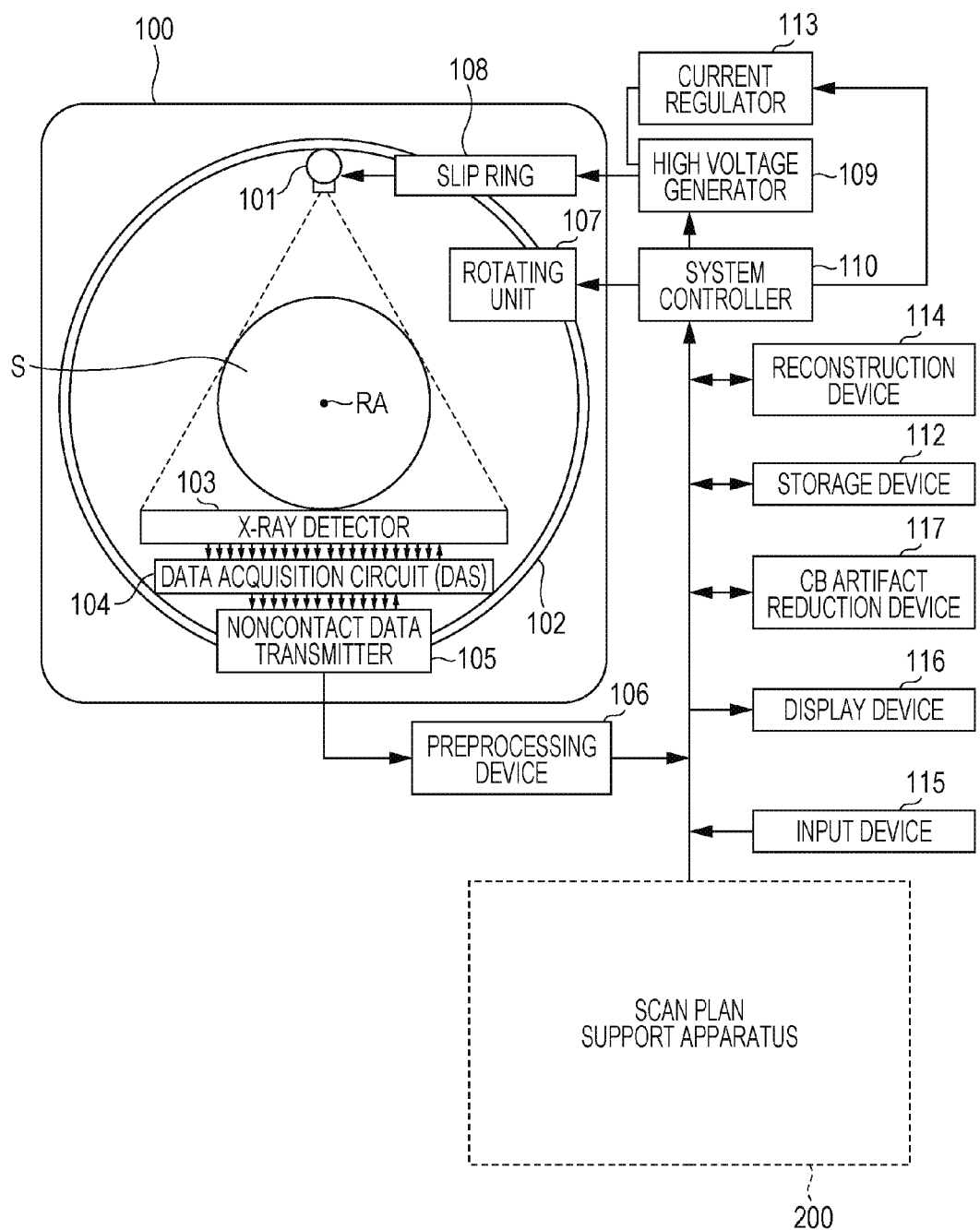
FIG. 1 is a diagram illustrating one embodiment of the multi-slice X-ray CT apparatus or scanner for substantially reducing cone-beam artifacts in images reconstructed from data acquired over circular trajectory according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116, multi-scale processing device 117 and the scan plan support apparatus 200. The scan plan support apparatus 200 includes a function for supporting an imaging technician to develop a scan plan.

One embodiment of the reconstruction device 114 further includes various software and hardware components and performs a predetermined analytic reconstruction process on the projection data. According to one aspect of the current invention, the reconstruction device 114 of the CT apparatus advantageously reconstructs an image volume by using a predetermined filtered backprojection (FBP) technique.

According to another aspect of the current invention, the reconstruction device 114 of the CT apparatus advantageously minimizes total variation (TV) using an iterative reconstruction technique. In general, the reconstruction device 114 in one embodiment of the current invention operates the total volume iterative reconstruction (TVIR) algorithm, which performs on the projection data simultaneous algebraic reconstruction such an ordered subset simultaneous algebraic reconstruction technique (OS-SART) step and regularization such as a TV minimization step. The two steps are sequentially implemented in the main loop where a number of iterations were prescribed in one embodiment.

Before the TV minimization step, the projection data undergoes an ordered subsets simultaneous algebraic reconstruction technique (OS-SART). The projection data is grouped into a predetermined number of subsets N each having a certain number of views. During the ordered subsets simultaneous algebraic reconstruction technique (OS-SART), each subset may be sequentially processed in one embodiment. In another embodiment, a plurality of the subsets may be processed in parallel by taking advantage of certain microprocessor such as multiple central processing units (CPU) or a graphics processing unit (GPU). In the total variation (TV) minimization step, one embodiment of the reconstruction device 114 employs a line search strategy to search a positive step size so as to ensure the objective function of the current image volume to be smaller than that of the previous image volume.

During the ordered subsets simultaneous algebraic reconstruction technique (OS-SART), the reconstruction device 114 also performs two major operations. Namely, for each subset N, the reconstruction device 114 reprojects the image volume to form the computed projection data and backprojects the normalized difference between the measured projection and the computed projection data to reconstruct an updated image volume. In further detail, one embodiment of the reconstruction device 114 reprojects the image volume by using the ray tracing technique where no coefficient of the system matrix is cached. Moreover, one embodiment of the reconstruction device 114 simultaneously reprojects all rays in a subset, and this is optionally implemented in parallel. In the backprojection, one embodiment of the reconstruction device 114 uses a pixel-driven technique to back-project all of the normalized difference projection data in a subset to form the desired updated image volume. Because the reconstruction device 114 back-projects all ray sums, i.e., difference projection data, in a subset to form an image volume, this operation is also optionally implemented in parallel. These operations are applied to every subset N to complete a single OS-SART step. In addition, AWAD is optionally combined.

In addition to the above described components, one embodiment of the current invention further includes various other software modules and hardware components for performing cone beam artifact reduction. According to one aspect of the current invention, a cone beam (CB) artifact reduction device 117 of the CT apparatus advantageously performs cone beam artifact reduction functions for substantially reducing cone beam artifacts under certain situations. In general, the CB artifact has two components including shading and high-contrast cone beams that degrade the image quality. To improve the image quality, shading is corrected by filtering rebinning while high-contrast is corrected by line image in one exemplary process.

In another embodiment of the current invention, the cone beam (CB) artifact reduction device 117 of the CT apparatus advantageously combines elements of exact reconstruction and iterative reconstruction such as SART to substantially reduce the cone beam artifact. As will be described in more detail, the reconstruction device 114 reconstructs a circular image from the measured projection data that has been acquired using a cone beam source over the circular source trajectory. Subsequently, the CB artifact reduction device 117 forward projects line data from the circular image, and then the reconstruction device 114 reconstructs a line image based upon the forward projected line data. Based upon the above steps, the CB artifact reduction device 117 combines the circular image and the line image. The combined image contains substantially reduced CB artifacts, which otherwise exist in a conventionally reconstructed image. Finally, the CB artifact reduction device 117 outputs the corrected image.

In one embodiment according to the current invention, the cone beam artifact reduction device 117 is operationally connected to other software modules and or system components such as the storage device 112, the reconstruction device 114, the display device 116 and the input device 115 via a data/control bus. In this regard, the cone beam artifact reduction device 117 alone does not necessarily perform the cone beam artifact reducing functions and or their associated tasks in other embodiments according to the current invention. Furthermore, the cone beam artifact reduction device 117 is optionally a part of other devices such as the reconstruction device 114 in alternative embodiments according to the current invention. Both the cone beam artifact reduction device 117 and the reconstruction device 114 are implemented in a variety of ways and are not limited to particular combination of software and hardware components.

Figure 2:
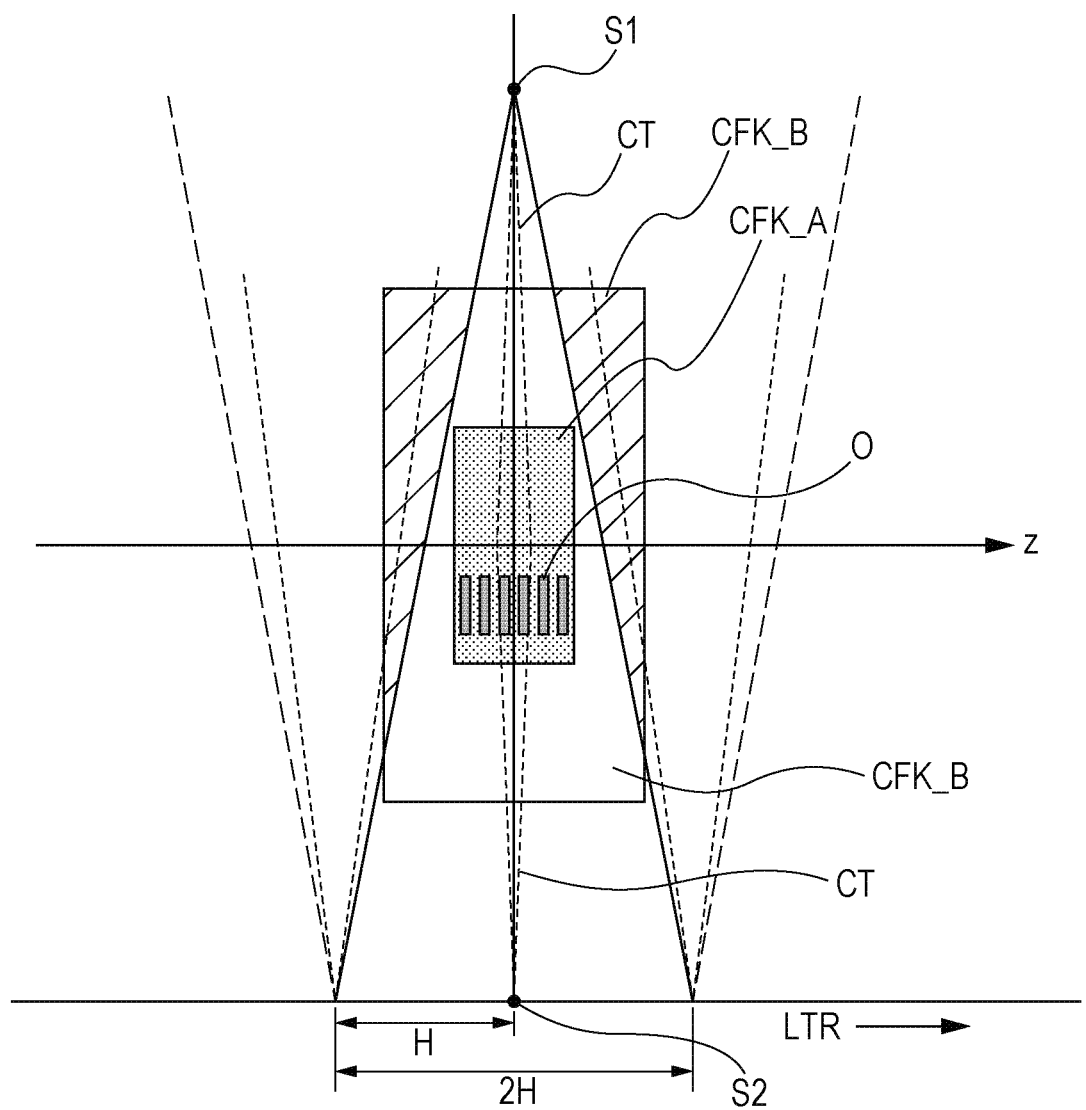
FIG. 2 is a diagram illustrating one aspect of the cause for cone beam (CB) artifacts to be substantially reduced by one embodiment according to the current invention.

FIG. 2 is a diagram illustrating one aspect of the cause for cone beam (CB) artifacts that are substantially reduced by one embodiment according to the current invention. The diagram illustrates an exemplary situation where a set of thin objects O is located at a relative position with respect to a source over a predetermined circular trajectory CT. Cone beam at a source position S1 emits toward the object O with a predetermined cone beam angle. The exemplary situation also illustrates that images are often reconstructed in a zoomed or desired field-of-view (FOV) with better resolution for a diagnostic purpose. Since information on an entire object attenuating the x-ray beam is necessary for forward projection, two volume images CFK_A and CFK_B are generated as illustrated in FIG. 2. The shaded areas correspond to insufficiently acquired measured data. The image CFK_A has the desired FOV to be used in a final result while the image CFK_B has a full FOV for generating missing line data. A required range 2H is shown along a line data direction LTR for generating the line data.

Figure 3:
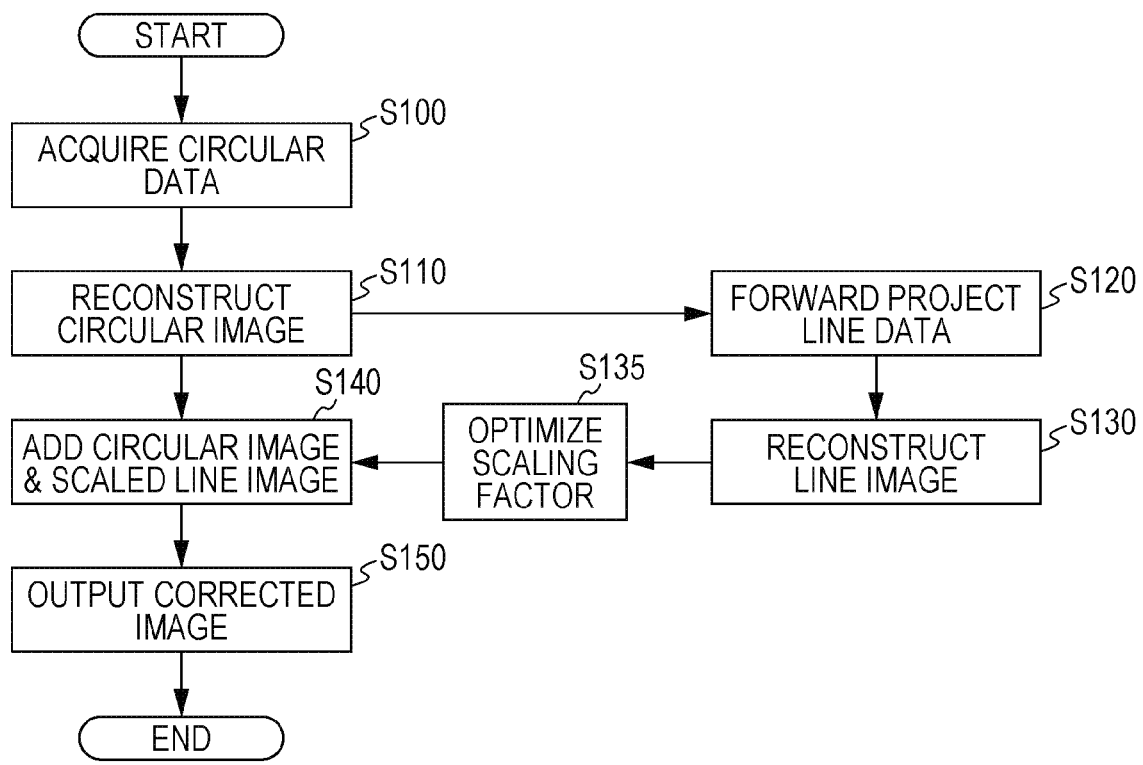
FIG. 3 is a flow chart illustrating general steps involved in an exemplary process of substantially reducing the cone beam (CB) artifacts using an adaptive scaling factor according to the current invention.

Now referring to FIG. 3, a flow chart illustrates general steps involved in an exemplary process of substantially reducing the cone beam (CB) artifacts using an adaptive scaling factor according to the current invention. In fact, the flow chart is a conceptual scheme of an exemplary process of substantially reducing the cone beam (CB) artifacts according to the current invention, and the current invention is not necessarily limited to the illustrated steps or acts as provided in the following description.

In a step S100, measured data is acquired with a cone beam source travelling over a predetermined circular trajectory. In general, the acquired measured data is susceptible to cone beam artifacts if an image is reconstructed in a conventional manner since the measured data is insufficient due to a cone beam circular scanning geometry. In a step S110, a circular image is reconstructed from the measured data that has been acquired using a cone beam source over a predetermined circular source trajectory. The reconstructed circular image is optionally stored in a predetermined storage to be retrieved later.

In steps S120 and S130, line data is generated and a line image is reconstructed from the generated line data. In a step S120, line data is forward projected or reprojected from the circular image that has been reconstructed in the step S110. The detail of the line data generation in the step S120 will be later described with respect to another exemplary flow chart. In a step S130, a line image is reconstructed based upon the forward projected line data that has been generated in the step S120.

A scaling factor $\alpha$ is optimized in a step S135. The scaling factor is applied to weigh the line image that has been reconstructed in the step S130. That is, a value of the scaling factor $\alpha$ is optimized to ultimately reduce the cone beam artifact in a final image in a substantial manner. The detail of the optimization of the scaling factor $\alpha$ will be further described with respect to another flow chart and diagram. In the step S135, the optimized scaling factor $\alpha$ is applied to the line image that has been reconstructed in the step S130 in order to generate a scaled line image.

Based upon the above steps S110, S120, S130 and S135, the circular image and the scaled line image are now combined in a step S140. The combined image contains substantially reduced CB artifacts, which otherwise exist in a conventionally reconstructed image. Finally, the corrected image is outputted in a step S150 for display or analysis. In another embodiment of the substantially reducing CB artifact, some of the above described steps are iteratively repeated using a known iterative technique such as SART to improve accuracy of the line data and in turn the artifact reduction in the outputted image.

Figure 4:
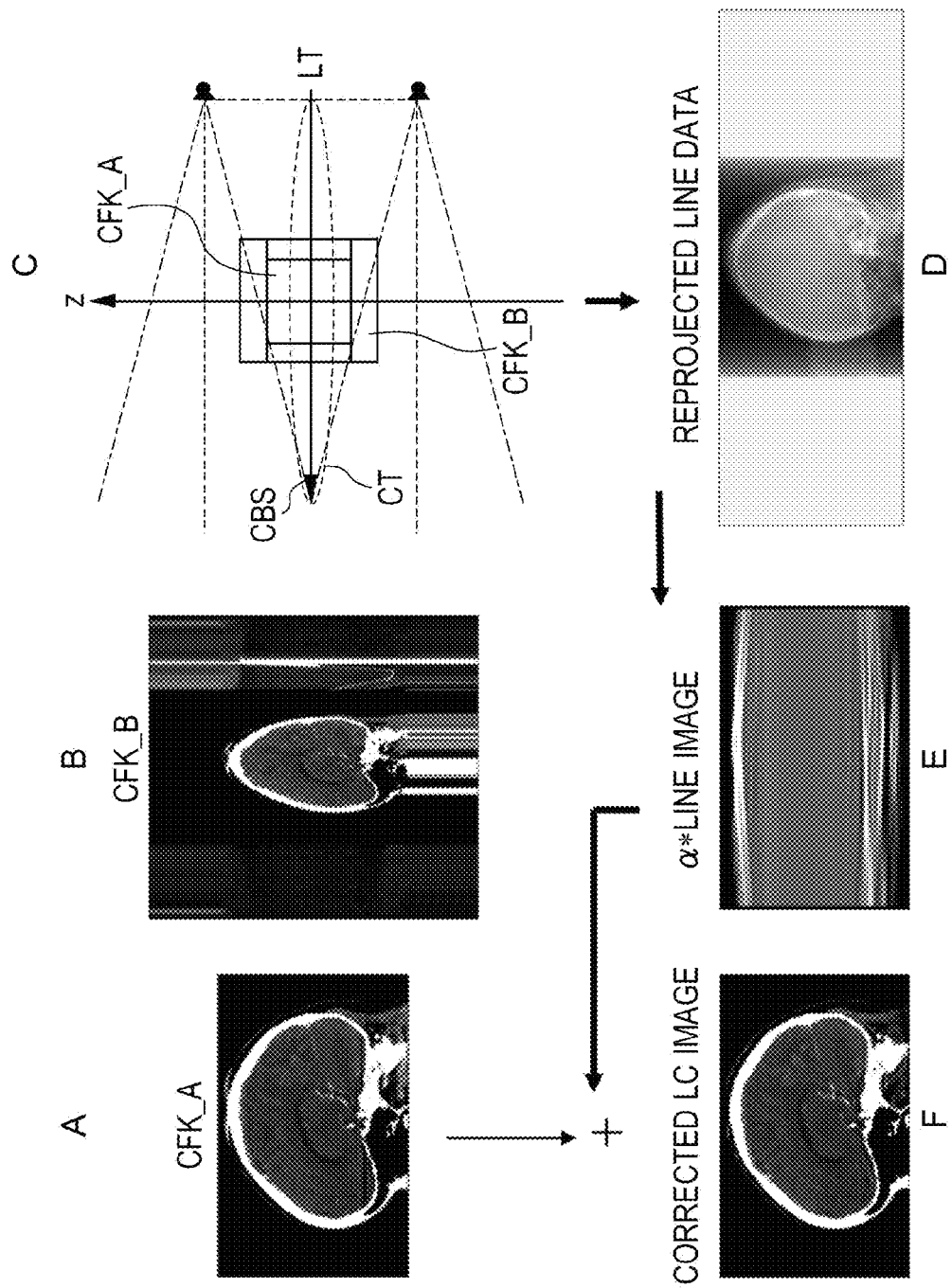
FIG. 4 is a collection of diagrams illustrating a certain conceptual solution for substantially reducing cone beam artifacts by using an adaptive scaling factor in one embodiment according to the current inventions.

FIG. 4 is a collection of diagrams illustrating a certain conceptual solution for substantially reducing cone beam artifacts by using an adaptive scaling factor in one embodiment according to the current inventions. As already described with respect to FIG. 2, an exemplary situation requires a zoomed or desired field-of-view (FOV) with better resolution for a diagnostic purpose. Since information on an entire object attenuating the x-ray beam is necessary for forward projection, a first image CFK_A and a second image CFK_B as illustrated in FIGS. 4A and 4B are reconstructed using circular Feld-Kamp (CFK) technique from corresponding circular data that is acquired using a cone beam source CBS over the circular trajectory CT as illustrated in FIG. 4C. FIG. 4C also illustrates that the circular data for the image volume CFK_A is a zoomed portion of the circular data for the image CFK_B. That is, the image CFK_A has a desired FOV within a full or large FOV of the image CFK_B, and the full FOV is extended along the Z axial direction.

According to one embodiment, the line data as illustrated in FIG. 4D is generated from forward projection of the filtered back-projected volume image CFK_B according to the current invention. In this regard, reprojection is synonymously used with forward projection in the above described line data generation in the current application. As described above, the second image CFK_B has a full FOV. Since x-rays with a large cone angle may pass through space in the Z direction beyond the reconstructed image, the image CFK_B is optionally extended over some Z-range that depends on the scanned system's cone angle. In other embodiments, to reduce the cone beam artifacts in the image CFK_B, a predetermined adaptive low-pass 3D filter is optionally applied to the image CFK_B before the forward projection along a line trajectory LT. Alternatively, a predetermined factorization approach is applied to the image CFK_B before the forward projection along a line trajectory LT in another embodiment.

After the line data is obtained by reprojection of the second image CFK_B from line trajectory, a line image with the desired FOV as illustrated in FIG. 4E is reconstructed from the line data as illustrated in FIG. 4D in one embodiment of the cone beam artifact reduction process or system according to the current invention. At the same time, the reconstructed line image is weighed by a predetermined scaling factor $\alpha$ as also noted by the symbol in FIG. 4E. The value of the scaling factor $\alpha$ is optimized before the application to the reconstructed line image based upon a predetermined technique that involves a cone beam artifact metric (CBAM) such as a total variation (TV), a standard deviation (SD) and a sum of squared difference (SSD). Since a predetermined cone beam artifact metric indicates strength of cone beam artifact that has been isolated from an image, an optimal value of the scaling factor is selected so that the optimal scaling factor value minimizes the cone beam artifact metric in a combined image by adding a correction image that has been scaled by the optimal value of the scaling factor. That is, the optimal value is adaptively determined based upon a predetermined rule rather than applying a uniform or fixed value.

Finally, the line image with the desired FOV that has been multiplied by the optimal value of the scaling factor $\alpha$ as illustrated in FIG. 4E is combined as indicated by a plus sign with the image volume CFK_A as illustrated in FIG. 4A to generate a corrected LC image as illustrated in FIG. 4F. The combined image LC has substantially reduced cone beam artifacts. In one embodiment, the image volume CFK_B is optionally updated by adding an image reconstructed from the line data with a full FOV. Furthermore, since the line data is forward projected from a volume image with artifacts, it is approximated data. For this reason, in another embodiment, an iterative approach is used to refine the line data and improve the cone beam artifact reduction.

Figure 5:
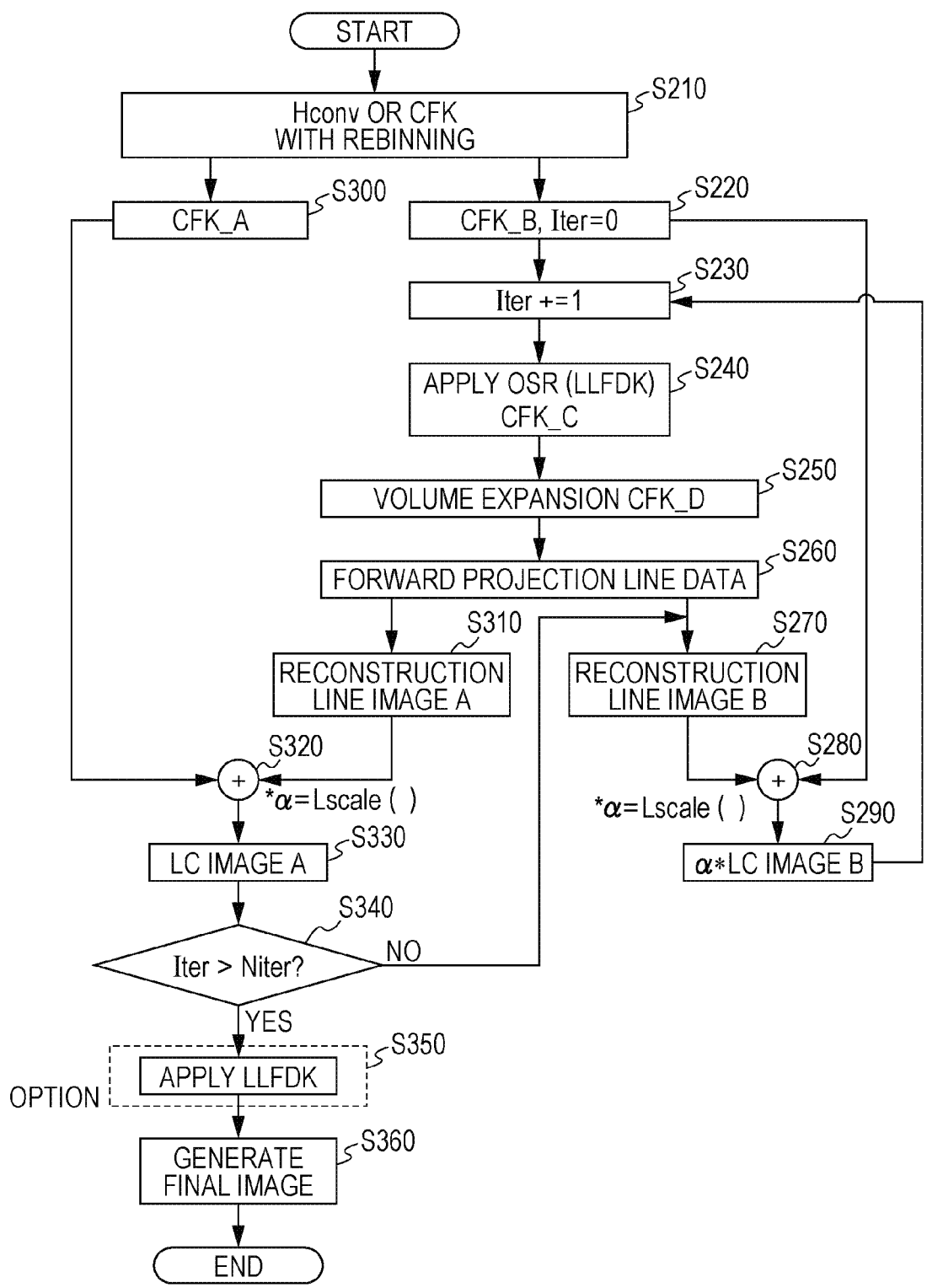
FIG. 5 is a flow chart illustrating steps involved in the cone beam artifact reduction process using an adaptive scaling factor in one embodiment according to the current invention.

FIG. 5 is a flow chart illustrating steps involved in the cone beam artifact reduction process using an adaptive scaling factor in one embodiment according to the current invention. In an exemplary process of substantially reducing cone beam artifacts by using an adaptive scaling factor, it is assumed that the measured data has been acquired by a predetermined circular data acquisition technique using a source travelling along a predetermined circular trajectory and having a certain conebeam angle. In general, the cone beam artifact reduction process in the embodiment generates two reference images CFK_A and CFK_B respectively having a small desired field of view and a full field of view from the corresponding circular cone beam data. The cone beam artifact reduction process in the embodiment generates synthetic data by forward projecting the reference image CFK_B having the full field of view along a predetermined source trajectory and then reconstructs a correction image from the synthetic data.

In one embodiment, the first image CFK_A and the second image CFK_B are ultimately combined to provide a combined image whereas the first image CFK_A contains cone beam artifacts while the second image CFK_B includes correction that is scaled by a scaling factor according to the current invention.

The correction is achieved by a combination of certain aspects of the implemented method and system according to the current invention. One aspect of correction is achieved because the predetermined source trajectory such as a line trajectory supplements the circular source trajectory of the reference image CFK_B. Furthermore, the cone beam artifact reduction process in the embodiment iteratively repeats certain steps such as steps S230 through S290 with respect to the line image so that a corrected image after a step S360 has substantially reduced cone beam artifacts according to the current invention. In alternative embodiments, the cone beam artifact reduction process performs line image manipulation in a predetermined manner in lieu of iteration.

Another aspect of correction is achieved by adaptively optimizing a value of the scaling factor α according to a predetermined optimization function such as Lscale ( ) according to one embodiment or process of the current invention. An optimized valued of the scaling factor α is determined in a variety of manners and is not limited to a particular function such as Lscale ( ). Furthermore, an optimized valued of the scaling factor α is optionally determined for each instance of iteration and or each of a first reference image CFK_A and a second reference image CFK_B. With respect to FIGS. 6 and 7, a few exemplary processes and systems will be described for optimizing a value of the scaling factor α according to the current invention.

Still referring to FIG. 5, the exemplary process of substantially reducing the cone beam artifact with an adaptively optimized value of the scaling factor α is further described in detail by referring to its steps according to the current invention. In general, reference images are obtained based upon a filtered-backprojection algorithm by filtering along predetermined filtering directions that are given by Cseg+ z/cos (gamma), where gamma is a cone angle, z is a vertical distance from Cseg, which is defined by a number of detector rows—1 divided by 2. In a step S210, the measured data undergoes a predetermined Hconv step, which outputs the convolved data to reconstruct two reference images. In one embodiment, the Hconv step utilizes hybrid Ramp plus Hilbert kernels. In another embodiment, the circular Feld-Kamp (CFK) technique is used to generate the two reference images. Additionally, a rebinning step is optionally added to the Hconv step to improve some image quality such as in brain shading for head imaging. In an alternative embodiment, a rebinning step and an inverse rebinning of the convolved data are optionally performed respectively prior and subsequent to the Hconv step to improve some image quality.

Subsequently, two reference images are generated. In a step S300 of one exemplary process, a first reference image CFK_A is reconstructed from the circular cone beam data using the circular Feld-Kamp (CFK) technique, and the first reference volume image CFK_A has a first field of view (FFOV). The FFOV is generally a desired back projection field of view. Similarly, in a step S220 of one exemplary process, a second reference image CFK_B is reconstructed from the circular cone beam data, and the second reference volume image CFK_B has a second field of view (SFOV), which is larger than the FFOV and optionally covers a gantry of the CT imaging system. Both of the first and second reference images CFK_A and CFK_B are now optionally stored in the respective steps S300 and S220 for later retrieval. Furthermore, the step S220 also initializes an iteration counter Iter for the subsequent instances of the steps involved in iteration.

Still referring to FIG. 5, iterative steps in the process of substantially reducing the cone beam artifact with an adaptively optimized value of the scaling factor α are further described in detail. In a step S230, the iteration counter Iter is incremented by one to keep track of a current instance of iteration with respect to a predetermined total number of iterations. In a step S240, a predetermined filter such as OSR filter is optionally applied to the second reference volume image CFK_B to generate an image CFK_C, which is a LLFDK-corrected CFK image. Subsequently, the image CFK_C is now volume expanded to an expanded slice CFK_D prior to forward projection in a step S250. In a step S260, the slice CFK_D is forward projected to line data, and the same line data is respectively reconstructed to a line image A and a line image B in a step S310 and a step S270.

Subsequently, the line image B is scaled by a line imaging scaling factor α in a step S270 for each iteration, and an optimal value of the line imaging scaling factor α is determined according to a predetermined technique so that the optimal scaling factor value minimizes a predetermined cone beam artifact metric in a combined image by adding a correction image that has been scaled by the optimal value of the scaling factor. Finally, the optimally scaled line image B is combined with the second reference image CFK_B in a step S280 to generate an optimally corrected α*LC image B in a step S290 before starting a next iteration with the optimally corrected α*LC image B in the step S230, where the iteration counter Iter is incremented.

By the same token, the line image A is also scaled by the line imaging scaling factor α in the S310 for each iteration, and an optimal value of the line imaging scaling factor α is determined according to a predetermined technique so that the optimal scaling factor value minimizes a predetermined cone beam artifact metric in a combined image by adding a correction image that has been scaled by the optimal value of the scaling factor. Finally, the optimally scaled line image A is combined with the first reference image CFK_A in a step S320 to generate an optimally corrected α*LC image A in a step S330.

With respect to the optimally corrected α*LC image A, it is determined whether or not a value of the iteration counter Iter is larger than a predetermined maximal number of iterations Niter in a step S340. If it is determined in the step S340 that the Iter counter value is not larger than the max iteration value Niter, the predetermined number of iterations has not yet been completed, and the process of substantially reducing the cone beam artifact proceeds to the step S260 for further iteration. On the other hand, if it is determined in the step S340 that the Iter counter value is larger than the max iteration value Niter, the predetermined number of iterations has been completed, and the process of substantially reducing the cone beam artifact optionally apply the LLFDK-correction in a step S350 before generating a corrected final image in a step S360. The process of substantially reducing the cone beam artifact with an adaptively optimized value of the scaling factor α is not limited to the above described steps or acts and includes other implementation steps according to the current invention.

Figure 6:
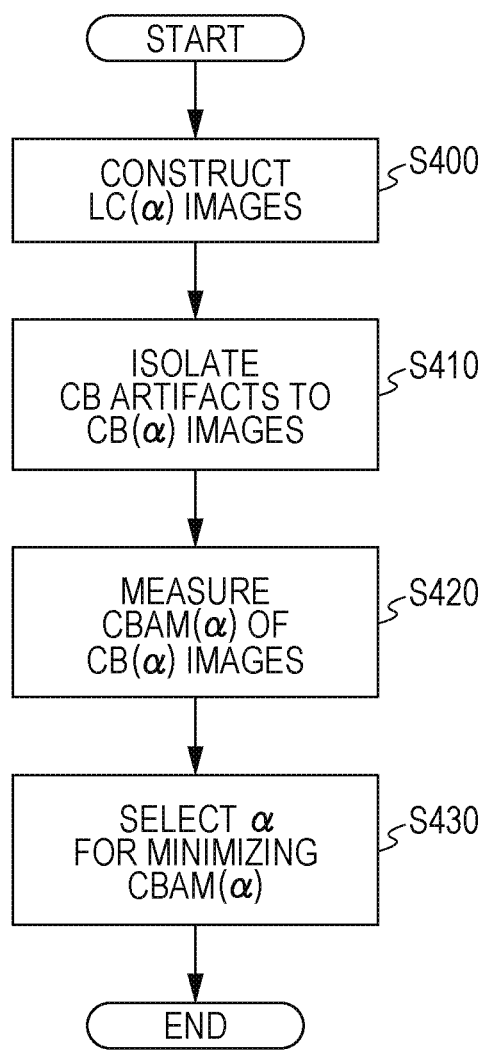
FIG. 6 is a flow chart illustrating steps involved in optimizing an adaptive scaling factor for in a cone beam artifact reduction process in one embodiment according to the current invention.
Figure 7A:
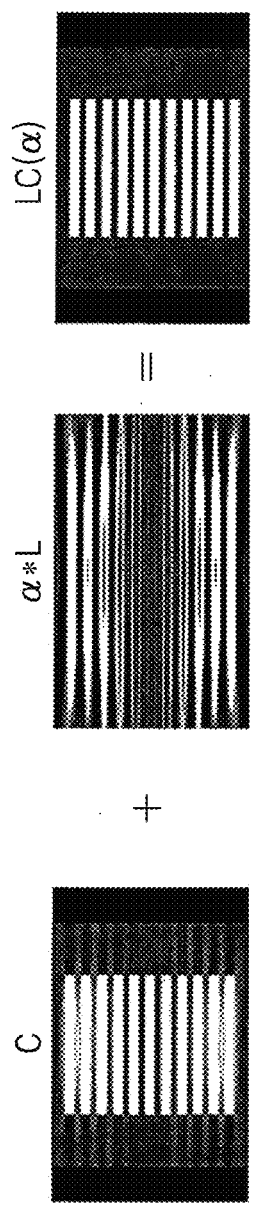
FIG. 7A illustrates one exemplary reduction of cone beam artifact based upon the scaling factor $\alpha$.

Now referring to FIG. 6, a flow chart illustrates steps involved in optimizing an adaptive scaling factor for in a cone beam artifact reduction process in one embodiment according to the current invention. The corrected images LC(α) is determined by CFK+αL, where CFK is a reference image and L is a line image generated from the reference image CFK, which is reconstructed from circular cone beam data by a predetermined reconstruction algorithm such as the circular Feld-Kamp (CFK) technique. In this regard, one exemplary reduction of cone beam artifact based upon the scaling factor α is illustrated in FIG. 7A.

Figure 7B:
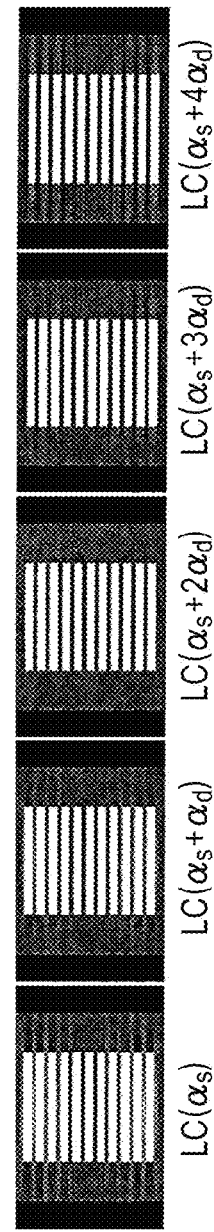
FIG. 7B illustrates one exemplary series of the corrected images $LC(\alpha)$.

In one embodiment of the process of reducing cone artifacts as illustrated in FIG. 6, an optimal value of the scaling factor is adaptively determined by initially constructing a predetermined number of corrected images LC(α) in a step S400. A scaling factor α is defined to be $\alpha_S \le \alpha \le \alpha_E$, wherein the α values are predetermined between a start scaling value $\alpha_S$ and an end scaling value $\alpha_E$ with a step value of $\alpha_d$. In this regard, one exemplary series of the corrected images LC(α) is illustrated in FIG. 7B.

Figure 7C:
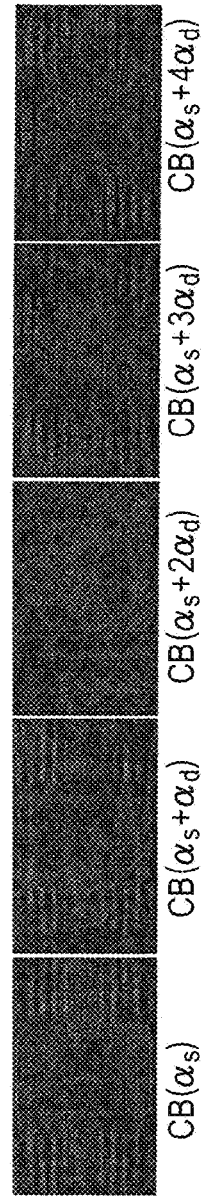
FIG. 7C illustrates one exemplary series of the cone beam artifact images $CB(\alpha)$.

To find an optimal value of the line scaling factor α, the cone beam artifact is isolated and the strength is analyzed using a predetermined cone beam artifact metric. In a step S410, the cone beam artifact is isolated from each of the series of the corrected images LC(α) into a corresponding one of cone beam images CB(α). That is, strength of the cone beam artifact is extracted into the cone beam images CB(α) for a subsequent analysis of optimizing the line scaling factor α in the following step. Optionally, a predetermined special filter such as the Adaptive Meian Z (AZF) filter is applied to the corrected images LC(α) for enhancing the cone beam artifacts prior to the extraction of the cone beam artifacts. In this regard, one exemplary series of the cone beam artifact images CB(α) is illustrated in FIG. 7C.

In a step 420, the strength of isolated cone beam artifact is compared using a predetermined cone beam artifact metric such as total variation (TV) in each of the cone beam images CB(α). That is, TV(CB(α)) is evaluated for each of the cone beam images CB(α). In one embodiment, TV is evaluated along only the z direction ($TV_Z$). In further detail, $TV_Z$ is defined as follows in Equation (1):

$$TV_z[A(ix, iy, iz)] = \frac{1}{N_x \times N_y \times N_z} \sum_{iz=0}^{N_z-1} \sum_{iy=0}^{N_y-1} \sum_{ix=0}^{N_x-1} |d_z| \quad (1)$$

Where $d_z = A(ix, iy, iz+1) - A(ix, iy, iz)$ $A = CB(\alpha)$

In another embodiment, TV is evaluated along the x, y and z directions ($TV_{XYZ}$). In further detail, $TV_{XYZ}$ is defined as follows in Equation (2):

$$TV_{xyz}[A(ix, iy, iz)] = \frac{1}{N_x \times N_y \times N_z} \sum_{iz=0}^{N_z-1} \sum_{iy=0}^{N_y-1} \sum_{ix=0}^{N_x-1} \sqrt{d_x^2 + d_y^2 + d_z^2} \quad (2)$$

Where $d_x = A(ix+1, iy, iz) - A(ix, iy, iz)$ $d_y = A(ix, iy+1, iz) - A(ix, iy, iz)$ $d_z = A(ix, iy, iz+1) - A(ix, iy, iz)$ $A = CB(\alpha)$ The above Equations (1) and (2) are merely illustrative, and the cone beam artifact metric is not limited by the equations. In fact, a cone beam artifact metric (CBAM) includes other metrics such as a standard deviation (SD) and a sum of squared difference (SSD) in addition to a total variation (TV) in order to practice the current invention.

In a step S430, an optimal value of the line scaling factor α is selected for minimizing the predetermined cone beam artifact metric. That is, after TV(CB(α)) is evaluated for each of the cone beam images CB(α), a value of the line scaling factor α is selected for minimizing TV(CB(α)). In the above described example as illustrated in FIGS. 7B and 7C, $TV_Z(CB(\alpha))$ is minimized when $\alpha=\alpha_S+2\alpha_d$ where $\alpha_S$ is a predetermined starting value and $\alpha_d$ is a predetermined stepping or increment value. Although the above described process is conceptually simplistic in its implementation, the implementation requires some level of computational intensity since a predetermined number of the corrected final images must be evaluated. A reduced number of samples of the original image is downsampled is also implemented. Even though it is downsampled for evaluating the final images, there may be a trade off between the computational efficiency and the accuracy in optimizing the scaling value. For example, input volume is 512×512, but is optionally downsampled to 128×128 grid. Then, it is necessary to compute the line image and or cone beam norm on the 128×128 grid.

Figure 8:
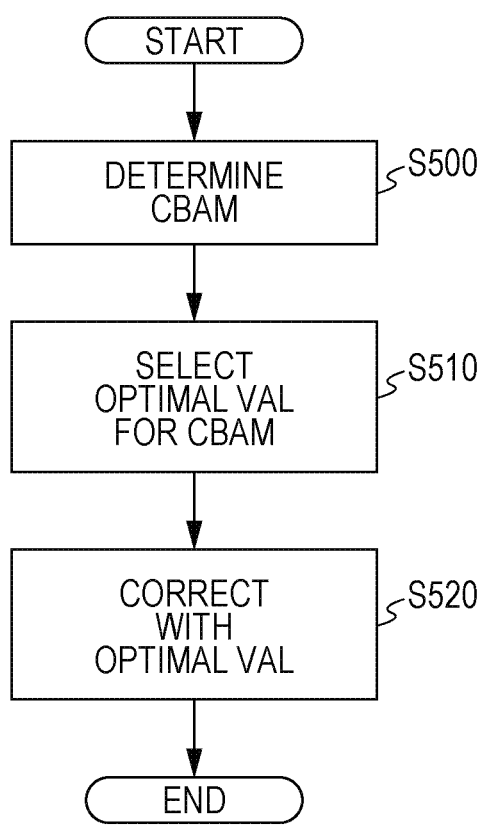
FIG. 8 is a flow chart illustrating steps involved in optimizing an adaptive scaling factor for in a cone beam artifact reduction process in another embodiment according to the current invention.

FIG. 8 is a flow chart illustrating steps involved in optimizing an adaptive scaling factor for in a cone beam artifact reduction process in another embodiment according to the current invention. One embodiment of optimizing an adaptive scaling factor as illustrated in FIG. 8 is implemented in a different manner from the process as illustrated in FIG. 6 by eliminating the evaluation of the final images. In general, after providing a combined image based upon a first image containing cone beam artifacts and a second image including correction that is scaled by a scaling factor, a cone beam artifact metric is determined for indicating strength of cone beam artifact that has been isolated from an image. An optimal value of the scaling factor is selected, and the selected optimal value minimizes the cone beam artifact metric in the combined image. Finally, the first image is corrected by adding the second image scaled by the selected optimal value of the scaling factor.

In further detail, steps of the flow chart in FIG. 8 are described with respect to some exemplary implementation. It is assumed that one embodiment of the process for substantially reducing cone beam artifact involves iterative steps as described with respect to FIG. 5. Furthermore, it is also assumed that circular FBP volume C(ix,iy,iz) and estimated line scan reconstructed volume $L^{(n)}(ix,iy,iz)$ at an iteration n are inputted or available prior to a step S500. Lastly, combined corrected volume $LC^{(n)}(ix,iy,iz)$ at an iteration n is outputted or available at the completion of the exemplary process. The combined corrected volume $LC^{(n)}$(ix,iy,iz) is defined by Equation (3) below:

$$LC^{(n)}(ix,iy,iz) = C(ix,iy,iz) + \alpha^*_n \times L^{(n)}(ix,iy,iz) \quad (3)$$

where $\alpha_n^*$ is the adaptive line scale factor or parameter whose value is to be optimized for ultimately reducing cone beam artifact in the combined corrected volume $LC^{(n)}$(ix,iy,iz). The adaptive line scale factor $\alpha_n^*$ is defined by Equation (4) below:

$$\alpha_n^* = \arg\min_\alpha \|C + \alpha L^{(n)}\|_{CB} \quad (4)$$

To determine the combined corrected volume $LC^{(n)}$(ix,iy,iz) with the least amount of cone beam artifact, a cone beam artifact metric (CBAM) is determined in a step S500 for indicating strength of cone beam artifact that has been isolated from an image. The cone beam artifact metric in the embodiment is total variation (TV) as defined above in Equation (1) or (2). In addition to TV, the cone beam artifact norm is defined as below in Equation (5):

$$\|A\|_{CB} = TV[F[A]] \quad (5)$$

where $A = CB(\alpha)$ and F is a predetermined special filter such as the Adaptive Meian Z filter for enhancing the cone beam artifacts.

In a step S510, an optimal value of the adaptive line scale factor is determined by the following technique in one embodiment of the process or the system according to the current invention. That is, in the above described implementation, Equation (4) is solved for the adaptive line scale factor $\alpha_n^*$ to minimize the cone beam artifact metric in the combined image according to the current invention. By denoting $$U(\alpha) = \arg\min_\alpha \|C + \alpha L^{(n)}\|_{CB},$$

the solution is to find $$\alpha_n^* = \arg\min_\alpha U(\alpha).$$

One direct way to find a solution is to select a grid of values and pre-compute numbers $U_k = U(\alpha_k)$ and then to find a minimum value of $U_k$. Another way to find a solution is to utilize Secant method where initial values $\alpha_0$ and $\alpha_1$ are chosen and then next value is found by the following recurrence relation as indicated in Equation (6):

$$\alpha_{n+1} = \alpha_n - U(\alpha_n)\frac{\alpha_n - \alpha_{n-1}}{U(\alpha_n) - U(\alpha_{n-1})} \quad (6)$$

where an optimal value for the adaptive line scale factor $\alpha_n^*$ is selected when a value stops changing with respect to a predetermined terminating condition such as $|\alpha_{n+1} - \alpha_n| < \epsilon$, $\epsilon = 10^{-2}$. In another embodiment, a known another method such as Golden Section Method is utilized.

In a step S520, the above determined optimal value for the adaptive line scale factor $\alpha_n^*$ is used to correct the first image by adding the second image scaled by the selected optimal value of the scaling factor.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of substantially reducing cone beam artifacts, comprising:
   providing a predetermined number of corrected images based upon a first image containing cone beam artifacts and a second image including correction that is scaled by a scaling factor at a corresponding one of the predetermined number of distinct values;
   isolating the cone beam artifacts in a plurality of third images from each of the corrected images;
   determining a cone beam artifact metric for each of the third images; and
   selecting an optimal one of the distinct values for the scaling factor based upon the cone beam artifact metric.

2. The method of substantially reducing cone beam artifacts according to claim 1 wherein the second image is a line image.

3. The method of substantially reducing cone beam artifacts according to claim 1 wherein the cone beam artifact metric includes a total variation (TV), a standard deviation (SD) and a sum of squared difference (SSD).

4. The method of substantially reducing cone beam artifacts according to claim 3 wherein the TV is determined along at least Z direction.

5. The method of substantially reducing cone beam artifacts according to claim 1 wherein the first image and the second image are scaled down.

6. The method of substantially reducing cone beam artifacts according to claim 1 further comprising adaptively filtering the second image using a predetermined adaptive median filter.

7. A method of substantially reducing cone beam artifacts, comprising:
   providing a combined image based upon a first image containing cone beam artifacts and a second image including correction that is scaled by a scaling factor;
   determining a cone beam artifact metric indicating strength of cone beam artifact isolated from an image;
   selecting an optimal value of the scaling factor that minimizes the cone beam artifact metric in the combined image; and
   correcting the first image by adding the second image scaled by the optimal value of the scaling factor.

8. The method of substantially reducing cone beam artifacts according to claim 7 wherein the cone beam artifact metric includes a total variation (TV), a standard deviation (SD) and a sum of squared difference (SSD).

9. The method of substantially reducing cone beam artifacts according to claim 8 wherein the TV is determined along at least Z direction.

10. The method of substantially reducing cone beam artifacts according to claim 7 wherein the second image is a line image.

11. The method of substantially reducing cone beam artifacts according to claim 7 wherein the first image and the second image are downsampled.

12. The method of substantially reducing cone beam artifacts according to claim 1 further comprising adaptively filtering the second image using a predetermined adaptive median filter.

13. A system for substantially reducing cone beam artifacts, comprising:
   a reconstruction device for reconstructing a first image containing cone beam artifacts according to a predetermined reconstruction technique; and
   a cone beam artifact reduction device connected to said reconstruction device for generating a predetermined number of corrected images based upon the first image and a second image including correction that is scaled by a scaling factor at a corresponding one of the predetermined number of distinct values, said cone beam artifact reduction device isolating the cone beam artifacts in a plurality of third images from each of the corrected images, said cone beam artifact reduction device determining a cone beam artifact metric for each of the third images, said cone beam artifact reduction device selecting an optimal one of the distinct values for the scaling factor based upon the cone beam artifact metric.

14. The system for substantially reducing cone beam artifacts according to claim 13 wherein the second image is a line image.

15. The system for substantially reducing cone beam artifacts according to claim 13 wherein the cone beam artifact metric includes a total variation (TV), a standard deviation (SD) and a sum of squared difference (SSD).

16. The system for substantially reducing cone beam artifacts according to claim 15 wherein the TV is determined along at least Z direction.

17. The system for substantially reducing cone beam artifacts according to claim 13 wherein the first image and the second image are downsampled.

18. The system for substantially reducing cone beam artifacts according to claim 13 wherein said cone beam artifact reduction device further comprises an adaptively filtering device for adaptively filtering the second image using a predetermined adaptive median filter.

19. A system for substantially reducing cone beam artifacts, comprising:
   a reconstruction device for reconstructing a first image containing cone beam artifacts according to a predetermined reconstruction technique; and
   a cone beam artifact reduction device connected to said reconstruction device for generating a combined image based upon the first image and a second image including correction that is scaled by a scaling factor, said cone beam artifact reduction device determining a cone beam artifact metric indicating strength of cone beam artifact isolated from an image, said cone beam artifact reduction device selecting an optimal value of the scaling factor that minimizes the cone beam artifact metric in the combined image, said cone beam artifact reduction device correcting the first image by adding the second image scaled by the optimal value of the scaling factor.

20. The system for substantially reducing cone beam artifacts according to claim 19 wherein the cone beam artifact metric includes a total variation (TV), a standard deviation (SD) and a sum of squared difference (SSD).

21. The system for substantially reducing cone beam artifacts according to claim 20 wherein the TV is determined along at least Z direction.

22. The system for substantially reducing cone beam artifacts according to claim 19 wherein the second image is a line image.

23. The system for substantially reducing cone beam artifacts according to claim 19 wherein the first image and the second image are scaled down.

24. The system for substantially reducing cone beam artifacts according to claim 19 wherein said cone beam artifact reduction device further comprises an adaptively filtering device for adaptively filtering the second image using a predetermined adaptive median filter.

25. The method of substantially reducing cone beam artifacts according to claim 1 wherein the scaling factor is optimized along Z direction.

* * * * *